US006551080B2

(12) United States Patent
Andersen et al.

(10) Patent No.: US 6,551,080 B2
(45) Date of Patent: Apr. 22, 2003

(54) UNSYNCHRONIZED PHASE OPERATION OF PERISTALTIC PUMP ROLLERS

(75) Inventors: John G. Andersen, Lupinvej 11, Blovstrød, Allerød (DK), 3450; Per Baron Brekke, Birkerød (DK)

(73) Assignee: John G. Andersen, Allerød (DK)

( * ) Notice: Subject to any disclaimer, the term of this patent is extended or adjusted under 35 U.S.C. 154(b) by 0 days.

(21) Appl. No.: 10/007,329

(22) Filed: Nov. 8, 2001

(65) Prior Publication Data

US 2002/0064470 A1 May 30, 2002

Related U.S. Application Data

(63) Continuation of application No. PCT/DK00/00233, filed on May 9, 2000.

(30) Foreign Application Priority Data

May 12, 1999 (DK) .......................................... 1999 00651

(51) Int. Cl.⁷ ................................................. F04B 43/12
(52) U.S. Cl. ............................... 417/477.11; 417/477.9; 417/477.7
(58) Field of Search .................. 417/477.11, 477.9, 417/477.7, 477.1, 476, 474

(56) References Cited

U.S. PATENT DOCUMENTS

| | | | | |
|---|---|---|---|---|
| 3,787,148 A | * | 1/1974 | Kopf | 417/477.9 |
| 4,363,609 A | * | 12/1982 | Cosentino et al. | 417/477.7 |
| 4,432,707 A | * | 2/1984 | Anderson et al. | 417/477.7 |
| 4,564,342 A | | 1/1986 | Weber et al. | 417/477 |
| 4,925,376 A | * | 5/1990 | Kahler | 417/477.11 |
| 5,230,614 A | * | 7/1993 | Zanger et al. | 414/477.9 |
| 5,257,917 A | | 11/1993 | Minarik et al. | |
| 5,470,211 A | | 11/1995 | Knott et al. | 417/477 |

FOREIGN PATENT DOCUMENTS

| | | |
|---|---|---|
| DE | 2921066 | 11/1980 |
| DE | 3243784 | 5/1984 |
| DE | 3840259 | 5/1990 |
| DK | 89039 | 5/1960 |
| DK | 147863 B | 10/1982 |

\* cited by examiner

Primary Examiner—Cheryl J. Tyler
(74) Attorney, Agent, or Firm—Winston & Strawn

(57) ABSTRACT

A peristaltic fluid pump having a suction side and a pumping side. The pump includes a pump housing having a mainly arcuate support surface, a flexible tube extending along this surface, a rotor having two opposite rollers for during operation rolling over the flexible tube along an entrance section where the tube is successively compressed, a pumping section extending across an angle of an arc of less than 180°, and an exit section where the compression successively ends, and a motor for during operation making the rotor rotate. The arcuate support surface is shaped in such a way that the rearmost and foremost rollers do not operate in synchronous phase opposition during their passage of the entrance and exit section. The peristaltic fluid pump is capable of pumping a fluid with less pressure difference and compressive pulsations in the fluid than previously known, making it especially suitable for pumping a patient's blood through a dialyzer.

18 Claims, 5 Drawing Sheets

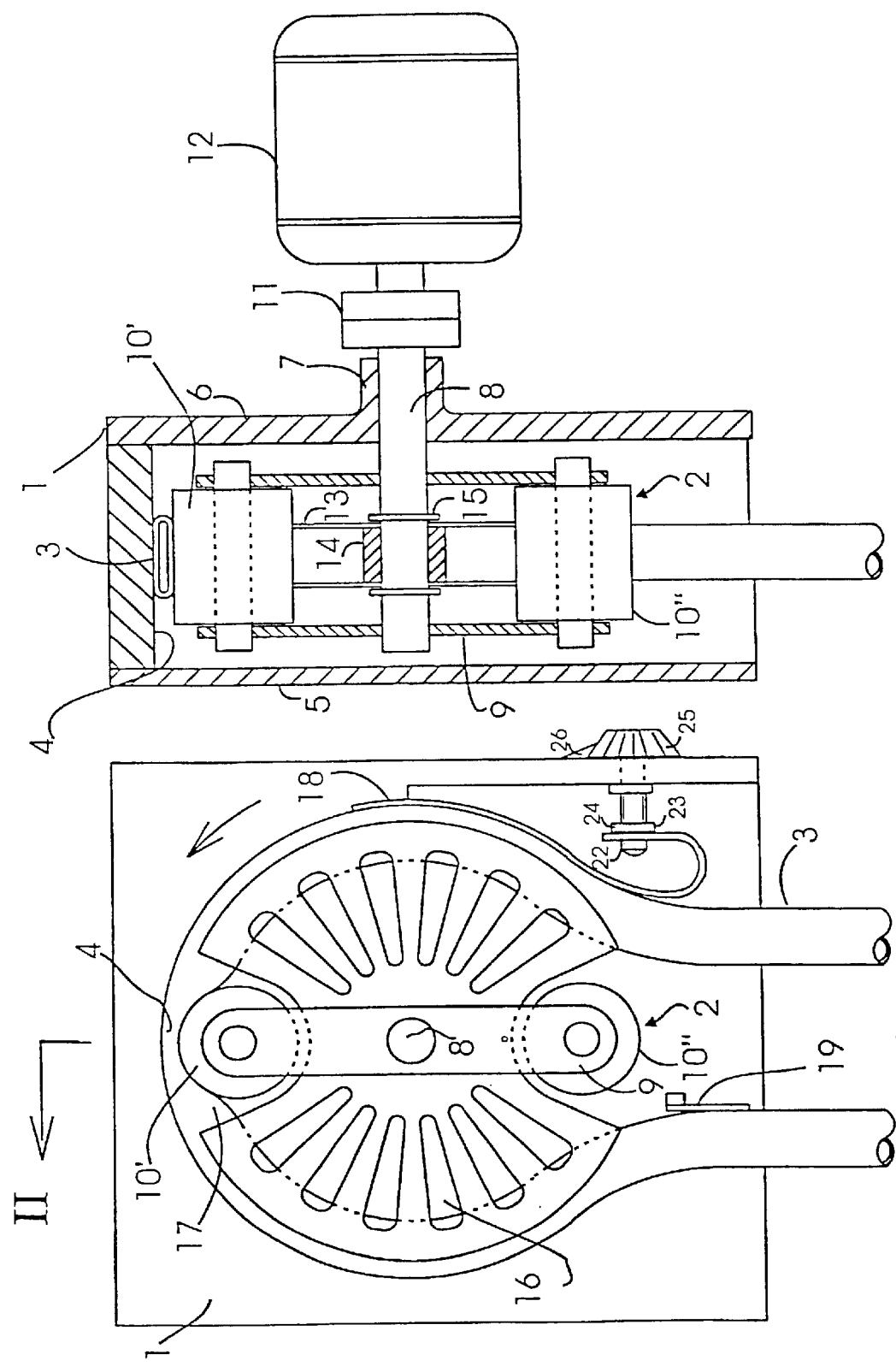

UNSYNCHRONIZED PHASE OPERATION OF PERISTALTIC PUMP ROLLERS

CROSS-REFERENCE TO RELATED APPLICATION

This application is a continuation of International Application PCT/DK00/00233 filed May 9, 2000, the content of which is expressly incorporated herein by reference thereto.

BACKGROUND ART

The invention relates to a peristaltic fluid pump having a suction side and a pumping side and of the kind that comprises a pump housing having a mainly arcuate support surface, a flexible tube extending along this surface, a rotor having two opposite rollers for during operation rolling over the flexible tube along an entrance section where the tube successively is compressed, a pumping section extending across an angle of an arc of less than 180°, and an exit section where the compression successively is ended, whereby both sections is having an idling zone, respectively, without pumping action and a pumping zone, respectively, with pumping action, means for during operation making the rotor rotate, that the arcuate support surface is constructed in such a way that the two opposite rollers do not operate in synchronous phase opposition during operation.

Such a peristaltic fluid pump is used among other things for hemodialysis of a patient with kidney insufficiency, the pump thus serving for pumping the patient's blood through a dialyzer.

Conventionally, a blood pump is arranged in such a way that both rollers can simultaneously be in pumping engagement with the flexible tube during operation. Thereby, the blood enclosed in the tube section between the rollers is subjected to a considerable positive pressure in relation to the wanted discharge pressure of the pump. When the leading roller is disengaged again from the tube, the positive pressure is relieved. The positive pressure and the compressive pulsations result in hemolysis of the red blood cells.

U.S. Pat. No. 3,787,148 discloses a peristaltic fluid pump having an arc-shaped bearing surface extending across a length of arc shorter than 180° and at the ends passing into symmetrically arranged, short ramps extending obliquely in towards the arc-shaped bearing surface. In the application, it is stated that one of the rollers thereby begins flattening the tube, at the same time as the other roller begins the opposite operation. However, this design is not able to prevent considerable positive pressure and compressive pulsations from being produced in the pumped fluid.

During fluid entrance into the entrance section, the rearmost roller successively displaces some of the fluid in the tube. The process corresponds to the process in a hydraulic pressure cylinder where a piston displaces fluid in a cylinder. The length of the entrance section will thereby correspond to the stroke of the piston.

However, the presence of the oblique ramps in the pump known from the above U.S. patent results in a short length of stroke with a quick displacement of the fluid under the roller. This quick displacement of fluid causes the creation of a compression wave in the tube.

The reverse process takes place in the exit section where the foremost roller quickly is pulled out of engagement with the tube and thereby leaves a space which just as quickly is filled with affluent fluid.

The oblique ramps thus add to the inclination of positive pressure and compressive pulsations being produced in the pumped fluid.

U.S. Pat. No. 3,787,148 is furthermore based on the condition that the process in the entrance section is outbalanced by the process operating in opposite directions in the exit section. That the fact is different in reality is due to the circumstance that the rearmost roller begins pressing in on a full tube while the foremost roller begins to disengage a flat tube and that the displaced fluid volume is increasing concurrently with the tube being compressed and decreasing concurrently with the compression being discontinued. When the foremost tube starts opening, there is furthermore a pressure difference over the opening corresponding to the difference between the feed pressure and the suction pressure. Such a pressure difference is not present at the simultaneous closing of the tube by the rearmost roller.

In this way, neither the conventional peristaltic pumps nor the pump known from U.S. Pat. No. 3,787,148 can function without considerable rises in pressure occurring in the fluid in a cyclically repetitive way.

U.S. Pat. No. 4,564,342 and U.S. Pat. No. 5,470,211 disclose other peristaltic pumps which both are arranged in such a way that the flexible tube is always fully occluded by one roller. Therefore these pumps are only able to operate with some compressive pulsations.

Thus, there is a need for new peristaltic pumps which avoid these problems, and the present invention now provides devices which satisfy this need.

SUMMARY OF THE INVENTION

The present invention provides a peristaltic fluid pump of the kind mentioned in the opening paragraph, that is arranged to pump a fluid with smaller pressure differences and compressive pulsations in the fluid than previously known. The pump also is arranged to be able to pump with a discharge pressure that is constant during an entire pump cycle.

These features and benefits are obtained in a peristaltic fluid pump having a suction side and a pumping side and which comprises: a pump housing having a mainly arcuate support surface, a flexible tube extending along the support surface, a rotor having two opposite rollers for during operation rolling over the flexible tube along an entrance section where the tube successively is compressed, a pumping section extending across an angle having an arc of less than 180°, an exit section where the compression successively is ended, and means for rotating the rotor during operation. Advantageously, the entrance and exit sections include an idling zone that does not provide a pumping action, and a pumping zone that does provide a pumping action. Also, the arcuate support surface is constructed in such a way that the two opposite rollers do not operate in synchronous phase opposition during operation, and the entrance section end and the exit section beginning are arranged at an angle that is smaller than 180°.

Preferably, the arcuate support surface is arranged in such a way that the rearmost roller enters into the pumping zone of the entrance section sufficiently to build up pressure between the rollers to a level which is the same as the pumping pressure, and the pumping zone of the exit section terminates at an angle of an arc ($\beta$) of more than 180° in relation to the pumping zone of the entrance section. It is beneficial for the arcuate support surface to extend along a curve such that fluid displacement during the passage of the rollers along the entrance and exit sections of the tube changes linearly during operation.

In one embodiment, the pump includes pressure means for elastically pressing against the tube outside of the engagement of the rollers to maintain the tube in a predetermined shape. Preferably, the pressure means comprises springs, such as disc springs, placed on opposite sides of the tube.

In other embodiments, the pump can include a device for affecting the tube with a spring power in the entrance section of the tube, or a device for affecting the tube with a spring power in a zone downstream of the exit section of the tube.

BRIEF DESCRIPTION OF THE DRAWINGS

The invention will be explained in greater detail below, describing only exemplary embodiments with reference to the drawings, in which FIG. 1 is a side elevational view of a peristaltic pump according to the invention with the front cover removed, FIG. 2 is the peristaltic pump in FIG. 1 seen along the line II—II.

DETAILED DESCRIPTION OF THE PREFERRED EMBODIMENTS

Figure 3:
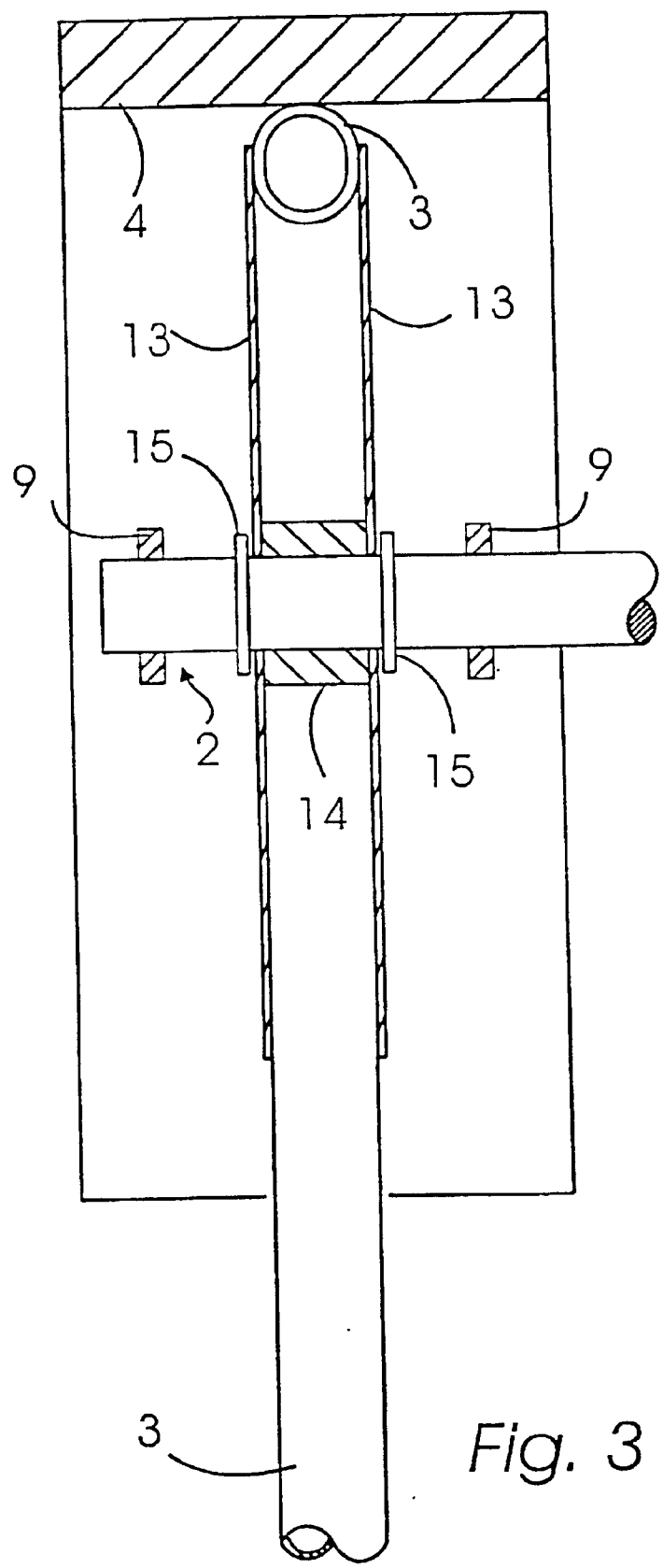
FIG. 3 is on a larger scale a fractional view of the pump in FIG. 2 but in a second pumping phase.

The novel and unique features according to the invention, whereby this is achieved, is due to the fact that the angle between the ending of the entrance section and the beginning of the exit section is smaller than 180°. Thereby, it is possible to compensate for the difference between the processes in the two sections and a constant feed pressure is advantageously obtained without compressive pulses in the fluid before or behind the foremost roller.

As mentioned above, fluid is successively displaced in the tube while the rearmost roller passes the entrance section. At the same time, the roller is forming an ever greater impression in the tube. The impression acts as a piston that pushes the fluid in front of it during the pump stroke. The roller is thus passing over the tube at the same rate as the fluid is flowing in this tube.

At first, the impression in the tube is not large enough to be able to create any noticeable pressure difference between the front and back of the impression. The pressure is equalized continuously via the still relatively large gap under the impression in the tube. There is, therefore, no pumping action in and through a zone which in the following is called the idling zone of the entrance section.

At a certain time, the impression will be so large that a pressure equalization no longer can take place between its front and back via the now relatively narrow gap in the tube under the roller. From this moment, the roller starts pumping at a pressure that rises from zero to full feed pressure along a zone which in the following is called the pumping zone of the entrance section.

The pumping zone of the entrance section passes continuously into the actual pump section of the tube, said section is extending into the exit section of the tube, and just as the entrance section the exit section has a pumping zone and an idling zone but evidently placed in reverse order in relation to the rotating direction of the rotor.

The foremost roller begins its opening operation with suction pressure at the back and feed pressure at the front. The pressure difference is inclined to make the fluid flow in the opposite direction than the wanted. This disadvantage is remedied by arranging the pump in such a way that the rearmost roller has reached so far into its pumping zone that it can equalize the above pressure difference before the foremost roller begins its opening operation.

The pressure equalization can expediently take place by arranging the end of the entrance and the beginning of the exit at an angle that is smaller than 180°.

Furthermore, the angle between the beginning of the entrance and the end of the pump section can advantageously be larger than 180°. Thereby, it is ensured that the foremost roller has time to draw the excess fluid from the successive compression of the tube by the rearmost roller with it during the passing of the pump section without significant rise in pressure on the suction side.

In order to avoid unwanted compressive pulsations when the fluid is pumped, both entrance and exit can be designed with a relatively great length to ensure the pump a long stroke and thereby a smooth and steady running.

The arcuate support surface can furthermore be extending in such a way that the fluid displacement increases and decreases respectively linearly during the passing of the entrance and exit section. This further ensures against compressive pulses being produced when the pump is operating.

The tube will usually be made of a suitable plastic. However, plastic is often deformed permanently when it repeatedly is subjected to heavy deformations. Thereby, the tube will gradually become more flat. Having this form, the volumetric displacement of the tube is not the same as before. The effective capacity of the pump will therefore gradually decline during use.

In order to avoid this unwanted effect the pump can be provided with pressure means for pressing against the sides of the tube and thereby forcibly keeping the tube in shape so that it outside the areas of engagement with the rollers always will contain the same quantity of fluid per unit length. This means that the volumetric displacement and the capacity of the pump always will be constant values.

The enforced shape of the tube can, for example, be an oval with a major axis perpendicular to the rotational axis of the rotor. When said pressure means furthermore are arranged in such a way that they are pressing elastically against the sides of the tube, the tube will serve as a buffer for absorbing possible compressive pulses in the fluid.

The pressure means can be any resilient member that applies force to the tube. In a simple and effective embodiment, two disc springs are disposed on opposite sides of the tube.

The pump can furthermore comprise a device, e.g. a spring, for affecting the tube with a spring force in the entrance section of the tube. This device acts as a kind of safety valve for preventing the pressure in the tube in exceeding a predetermined limit in the entrance phase of the rearmost roller.

The spring force of the spring can advantageously be adjustable so that the discharge pressure of the pump can be adapted to dialyzers with different flow resistance. Thereby the pump can be made to pump with the same output irrespective of the individual flow resistance of the current dialyzer.

The pump can furthermore comprise a device, e.g. a spring, for affecting the tube with a spring force in a zone downstream of the exit section of the tube. This device acts as a kind of non-return valve which reduces or prevents the tendency of the fluid running in the opposite direction than that which is desired.

The pump according to the invention can advantageously be used in many places, such as in industry for pumping corrosive fluids, or for pumping drinks, such as milk which has to meet a high hygienic standard.

The pump can also with great advantage be used as heart pump or for pumping a patient's blood through a dialyzer. The following description illustrates a preferred embodiment where the pump is a blood pump of the latter kind.

The main components of the blood pump in FIGS. 1 and 2 is a pump housing 1, a rotor 2 and a flexible tube 3.

Inside the housing 1 is constructed an arcuate support surface 4 for supporting the tube 3. At the front, the housing is closed with a front cover 5 and at the back with a back cover 6 provided with a bearing 7.

The rotor 2 is by means of a rotor shaft 8 flyingly journaled in a bearing 7 of the back cover. On the part of the shaft that is inside the housing, two parallel rotor arms 9 are mounted at a mutual distance. Equidistantly from the shaft 8, a roller 10' and 10" is rotatably journaled at the ends of each of these rotor arms 9.

The part of the rotor shaft 8 that is extending out of the housing 1 is by means of a coupling 11 connected to a motor 12 for rotating the rotor during operation.

On the rotor shaft are furthermore mounted two disc springs 13 which are kept at a mutual distance by a spacer pipe 14 and locked on the shaft 8 by means of locking rings 15.

In each disc spring are constructed a number of radially extending cuts 16 for providing the desired spring characteristic, and furthermore two other cuts 17 for making room for the rollers.

During operation, the rotor is rotating anticlockwise as indicated with the arrow. At the entrance end of the rollers, the tube is supported by a spring 18 while the second spring 19 is pressing against the tube at the exit end.

As shown in FIGS. 4–9, the tube is during the entrance of the roller successively flattened to a pump configuration in which the roller is pumping blood through the tube. At the exit end the same process is taking place but in reverse order.

If a positive pressure and compressive pulsations are produced in the pumped blood, it can result in hemolysis of the red blood cells.

The spring 18 at the entrance end of the tube acts as a safety valve for preventing such a positive pressure in the tube. For this purpose, the spring 18 is arranged in such a way that it yields if the pressure in the tube exceeds a predetermined quantity.

As for the spring 19, it acts as a non-return valve for preventing backflow when the foremost roller begins its disengagement with the tube. The spring 19 is arranged in such a way that it more or less compresses the tube in case of drop of pressure. Thereby, a possible backflow is checked or prevented.

As can be seen best in FIG. 3, the disc springs 13 are pressing the tube oval. Thereby, its cross-sectional area is reduced in relation to a full, round tube so that the oval tube during the entrance of the rearmost roller can receive extra blood without any significant rise in pressure as the disc springs during this merely yield and allow the tube to assume its initial round shape.

The disc springs can for example be made of plain spring steel having a small friction factor in relation to the tube material. If desired, the springs can be Teflon-coated on the side facing the tube to reduce friction. Alternatively, the disc springs can be made of a plastic material such as Teflon. The cuts 16 in the disc springs serve for providing the springs with the necessary flexibility.

The embodiments of the springs 18, 19 and the disc springs 13 that are shown and described are only to be taken as examples as they within the scope of the invention can have any expedient design.

The disc springs 13 can thus be replaced by elastically deformable, curved strips made of a suitable resilient or cellular rubber. The strips elastically exert a pressure on the sides of the flexible tube and are during operation compressed simultaneously with tube during the passing of the rollers.

In the dialysis treatment, it is desirable that the dialyzer be adapted to the individual needs of the patient. The blood pump according to the invention is therefore likely to be used for dialyzers with different flow resistance. If the capacity of the blood pump still is to be kept at a fixed value, its discharge pressure must therefore be able to be adjusted in dependence of the flow resistance in the current dialyzer.

This adjustment advantageously takes place by means of an adjusting screw 22 for adjusting the value of the spring power of the spring. The screw 22 is as shown screwed into a nut 23 on a bent end 24 of the spring 19. On the opposite side the screw is provided with an adjustment knob 25 with a pointer 26 for indicating the current value of the spring power on a scale not shown.

FIGS. 4–9 illustrate how the entrance of a roller takes place. The exit takes place in reverse order.

Figure 4:
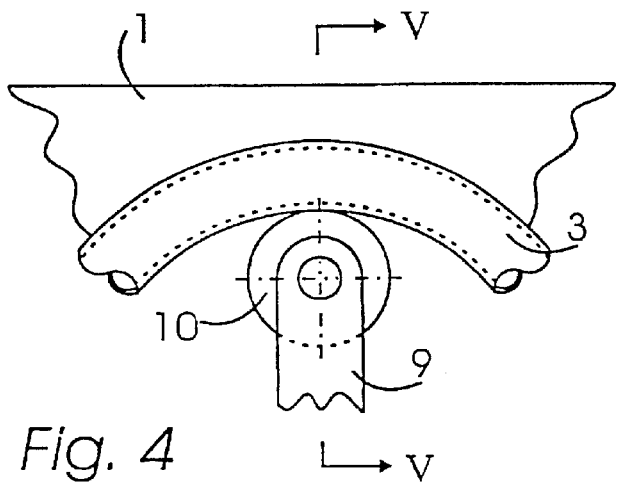
FIG. 4 is a fractional view of a roller which in a first pumping phase is rolling over the tube of the peristaltic pump.
Figure 5:
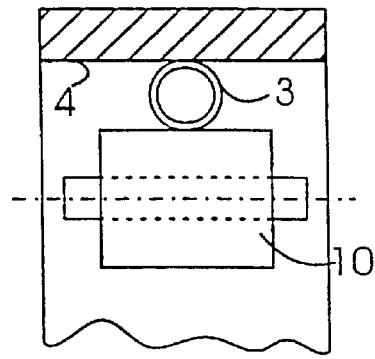
FIG. 5 is the roller in FIG. 4 seen along the line V—V.
Figure 6:
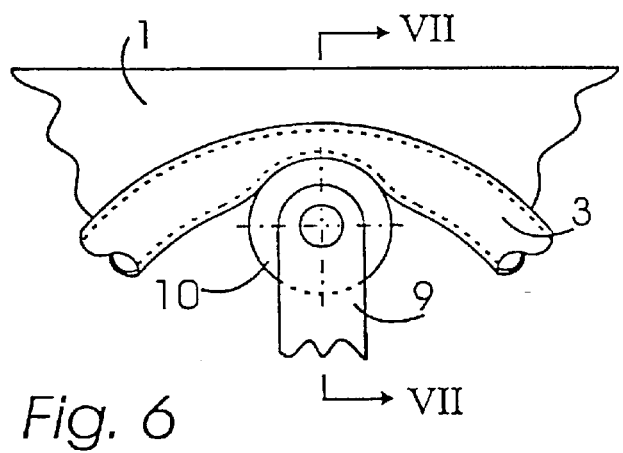
FIG. 6 is a fractional view of the roller in a second pumping phase.
Figure 7:
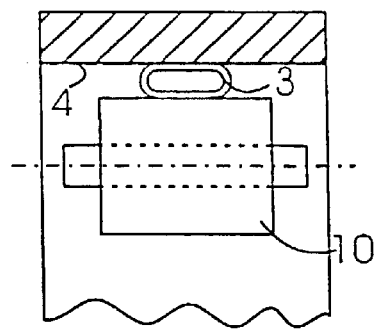
FIG. 7 is the roller in FIG. 6 seen along the line VII—VII.
Figure 8:
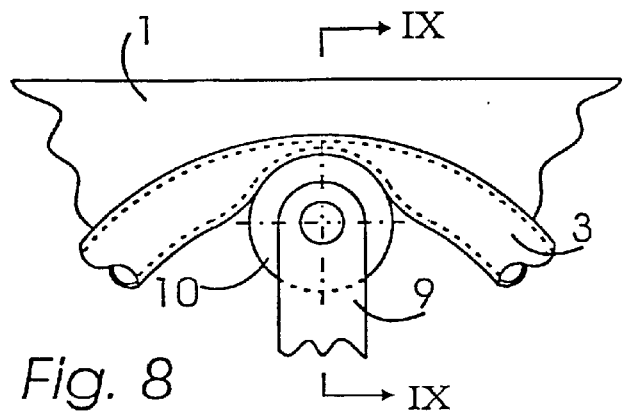
FIG. 8 is a fractional view of the roller in a third pumping phase.
Figure 9:
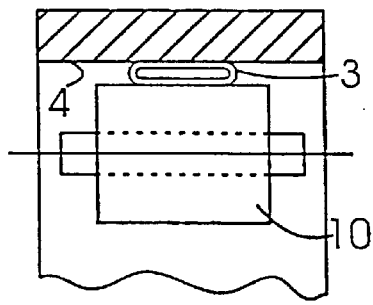
FIG. 9 is the roller in FIG. 9 seen along the line IX—IX.

In FIGS. 4 and 5 the roller 10 preliminarily touches the tube 3. There is no pumping action. The pumping action does not begin until the roller has compressed the tube sufficiently. It is assumed that this is the case in FIGS. 6 and 7. In FIGS. 8 and 9 a full pumping action is obtained. It is in this connection mentioned that the blood pump can function effectively even if the tube is not fully compressed. In some cases, it is however preferred to pump with the tube being completely compressed.

Figure 10:
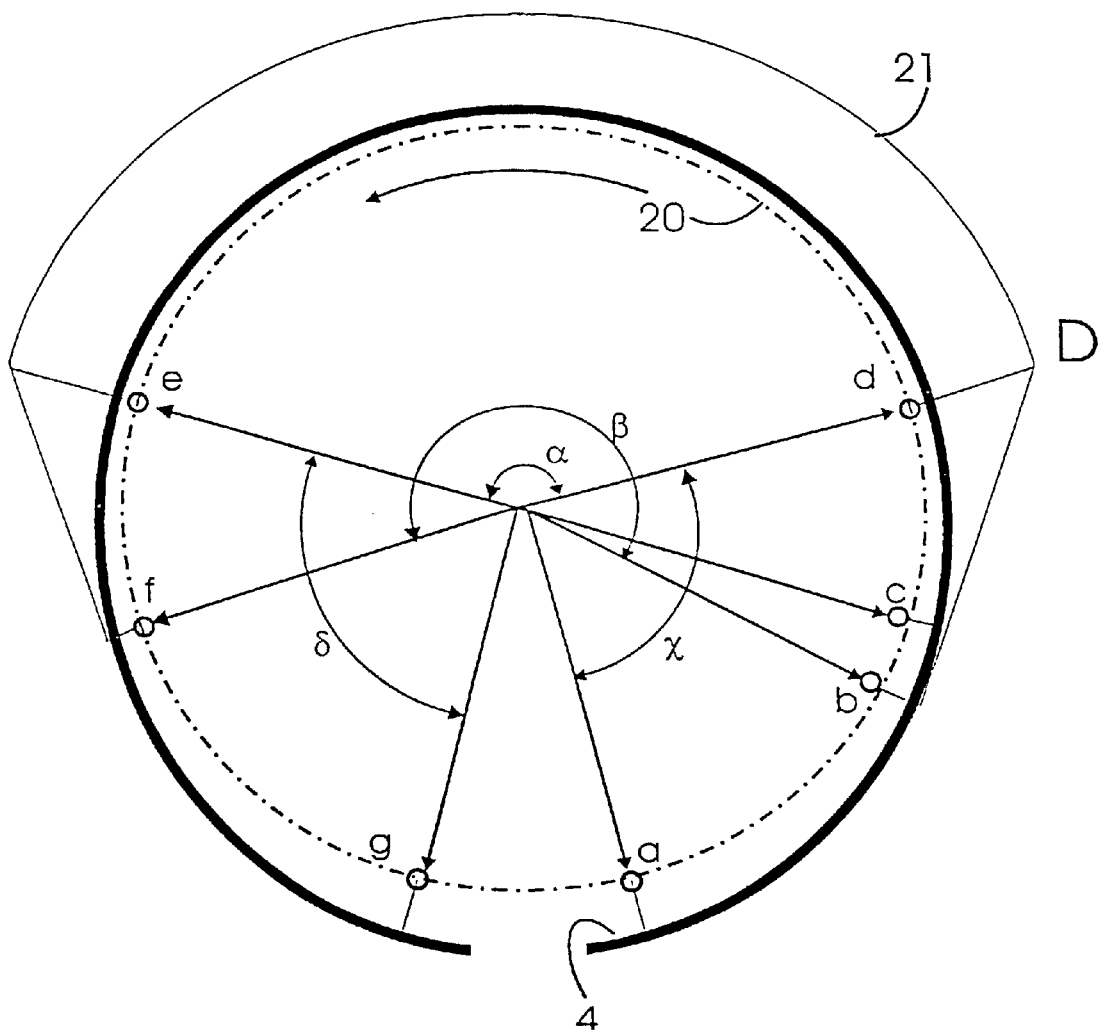
FIG. 10 is a diagrammatic view of the working cycles of the pump.

FIG. 10 diagrammatically illustrates the working cycles of the blood pump. The circular cycle described by the rollers is shown by dash-dot line 20. The arcuate support surface 4 is shown in full line, and the pressure produced by the respective roller during its passing is shown by light line 2 1. The rollers are illustrated by the shown arrows while the different pumping phases are indicated by the letters a-g. The rotor is rotating anticlockwise in the direction indicated by the arrow.

A roller begins its engagement with the flexible tube at point a in the position shown in FIGS. 4 and 5 and is in the same position disengaged at point g. The total stroke of the roller is thus the distance a-g.

At first, the tube is compressed so little that there is no pumping action. At b it is assumed that the situation in FIGS. 6 and 7 has taken place. The pumping action begins. At d the situation in FIGS. 8 and 9 has been reached. There is now full pumping action.

During the continuous rotation of the rotor there is now pumped at full power until the point e has been reached. Here the roller begins to open the tube. At f the situation in FIG. 7 has taken place again. The pumping action has ended. From f-g the roller gradually disengages the tube further but without pumping action. In g the roller only just touches the tube. From g-a the roller does not touch the tube.

The stroke a-g is thus divided into an entrance section a-d, a full pumping section d-e and an exit section e-g.

The entrance section a-d is further divided into an idling zone a-b and a pumping zone b-d, whereas the exit section e-g is divided into a pumping zone e-f and an idling zone f-g.

At e the foremost roller in some of the conventional blood pumps opens the tube with a feed pressure at the front and a suction pressure at the back. The pressure difference between these two pressures causes the blood to start flowing in the opposite direction of the wanted direction, that is clockwise in stead of counter-clockwise.

The working cycles of the blood pump are therefore according to the invention arranged in such a way that the diametrically opposite rearmost roller at c has entered so far into the pumping zone of the entrance section b-d that the roller has been able to built up the pressure between the foremost and rearmost roller to the same level as the pumping pressure.

Thereby backflow is prevented, and it is furthermore advantageously obtained that the blood pump will be pumping with constant discharge pressure.

A condition for obtaining this effect is that the angle a between the ending d of the entrance section and the beginning e of the exit section is smaller than 180°.

A second condition consists in the ending f on the pumping zone of the exit section being displaced an angle of an arc β of more than 180° in relation to the beginning b of the pumping zone in the entrance section.

It is important that the roller during the entrance is compressing the tube calmly and slowly so that harmful compressive impulses are avoided, and it is obviously just as important that the roller is disengaged again slowly and calmly from its engagement with the tube.

The entrance section a-d and the exit section e-g are therefore both extending across a length of arc χ;δ of between 130° and 30°, preferably between 110° and 50°, and especially between 100° and 70°.

In order to further ensure effectively against compressive impulses being produced in the pumped blood, the entrance section a-d and the exit section e-g, respectively are constructed in such a way that the displaced amount of blood is changed linearly during the passing of the rollers of each of these sections.

Figure 11:
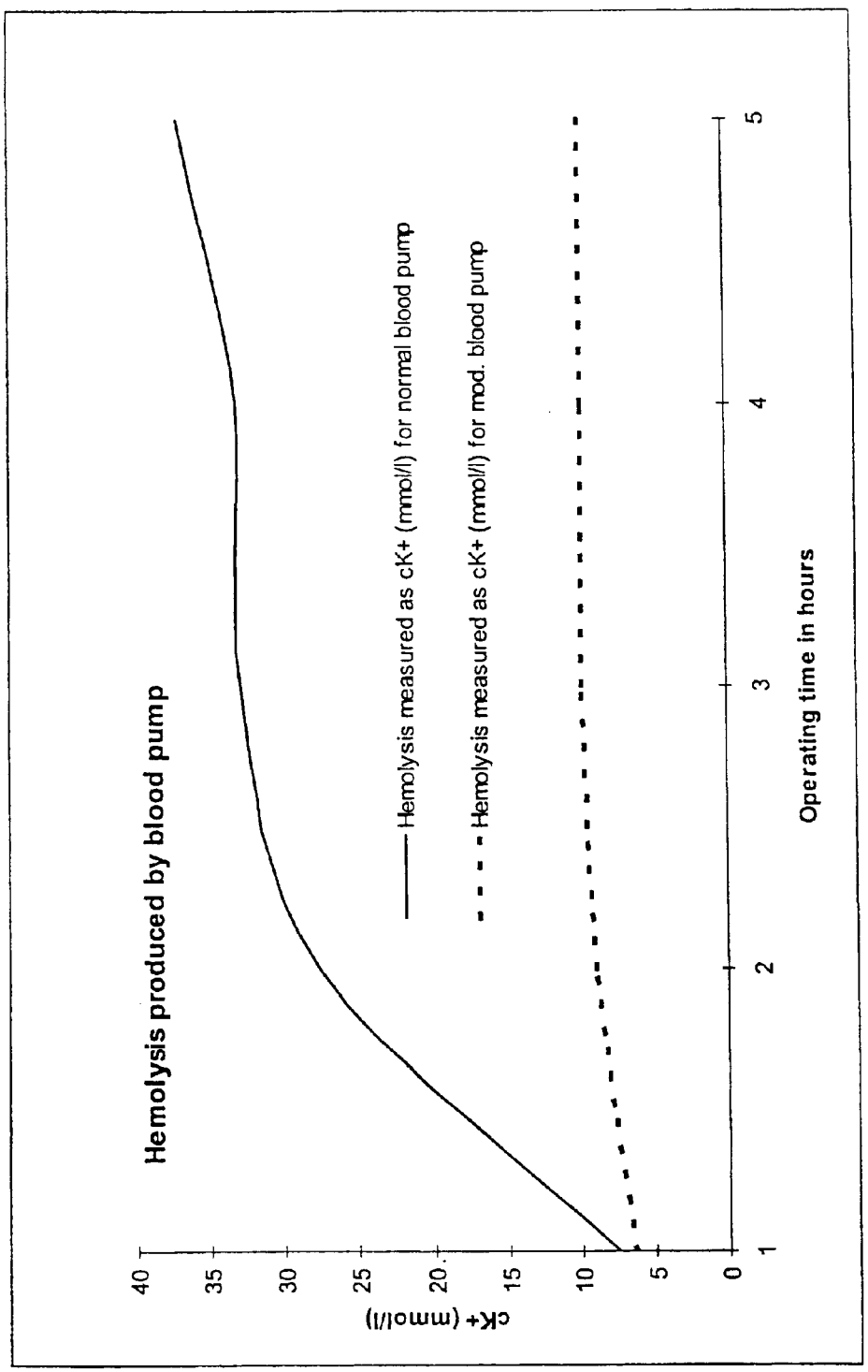
FIG. 11 is a graphic display of the hemolysis that was produced by using a conventional blood pump and a blood pump according to the invention, respectively.

FIG. 11 is a graphic display of the hemolysis that was produced by using a conventional blood pump and a blood pump according to the invention, respectively.

The test was in both cases carried out with the following:
Blood volume: 200 ml
Pumping rate: 300 ml/min
Na-heparin added: 70 ie/ml If hemolysis can be measured as change in amount of potassium, it is due to the fact that the red blood cells have a very high potassium content which at hemolysis (bursting of the cell membranes of the blood cells) are released to the blood plasma (serum) and thereby can be measured as an increasing potassium content.

As can be seen the hemolysis is decreased drastically when a blood pump according to the invention is used instead of a conventional blood pump.

What is claimed is:

1. A peristaltic fluid pump having a suction side and a pumping side, and comprising:
   a pump housing having a mainly arcuate support surface,
   a flexible tube extending along the support surface,
   a rotor having two opposite rollers for during operation rolling over the flexible tube along an entrance section where the tube successively is compressed, a pumping section extending across an angle having an arc of less than 180°, and an exit section where the compression successively is ended, whereby the entrance and exit sections include an idling zone that does not provide a pumping action, and a pumping zone that does provide a pumping action, and
   means for rotating the rotor during operation,
   wherein the arcuate support surface is constructed in such a way that the two opposite rollers do not operate in synchronous phase opposition during operation, the entrance section end and the exit section beginning are arranged at an angle that is smaller than 180°, and a fluid is pumped with a discharge pressure that is constant during an entire pump cycle and with minimum pressure differences and compressive pulsations in the fluid.

2. A peristaltic fluid pump according to claim 1, wherein the arcuate support surface is arranged in such a way that the rearmost roller enters into the pumping zone of the entrance section sufficiently to build up pressure between the rollers to a level which is the same as the pumping pressure.

3. A peristaltic fluid pump according to claim 1, wherein the pumping zone of the exit section terminates at an angle of an arc (β) of more than 180° in relation to the pumping zone of the entrance section.

4. A peristaltic fluid pump according to claim 1, wherein both the entrance section and the exit section have an arc length χ;δ of between 130° and 30°.

5. A peristaltic fluid pump according to claim 1, wherein both the entrance section and the exit section have an arc length χ;δ of between 100° and 70°.

6. A peristaltic fluid pump according to claim 1, wherein the arcuate support surface extends along a curve such that fluid displacement during the passage of the rollers along the entrance and exit sections of the tube changes linearly during operation.

7. A peristaltic fluid pump according claim 1, further comprising a device for affecting the tube with a spring power in the entrance section of the tube.

8. A peristaltic fluid pump according claim 1, further comprising a device for affecting the tube with a spring power in a zone downstream of the exit section of the tube.

9. A peristaltic fluid pump according to claim 1, wherein the rollers are configured to prevent positive pressure from building up in the flexible tube.

10. A peristaltic fluid pump according to claim 9, wherein each roller includes yielding means arranged in such a way to yield if the pressure in the flexible tube exceeds a predetermined quantity.

11. A peristaltic fluid pump having a suction side and a pumping side, and comprising:
   a pump housing having a mainly arcuate support surface,
   a flexible tube extending along the support surface,
   a rotor having two opposite rollers for during operation rolling over the flexible tube along an entrance section where the tube successively is compressed, a pumping section extending across an angle having an arc of less than 180°, and an exit section where the compression successively is ended, whereby the entrance and exit sections include an idling zone that does not provide a pumping action, and a pumping zone that does provide a pumping action, and means for rotating the rotor during operation, wherein the arcuate support surface is constructed in such a way that the two opposite rollers do not operate in synchronous phase opposition during operation, and both the entrance section end and the exit section have an arc length $\chi;\delta$ of between 110° and 50°.

12. A peristaltic fluid pump having a suction side and a pumping side, and comprising:

a pump housing having a mainly arcuate support surface, a flexible tube extending along the support surface, a rotor having two opposite rollers for during operation rolling over the flexible tube along an entrance section where the tube successively is compressed, a pumping section extending across an angle having an arc of less than 180°, and an exit section where the compression successively is ended, whereby the entrance and exit sections include an idling zone that does not provide a pumping action, and a pumping zone that does provide a pumping action, pressure means for elastically pressing against the tube outside of the engagement of the rollers to maintain the tube in a predetermined shape, and means for rotating the rotor during operation, wherein the arcuate support surface is constructed in such a way that the two opposite rollers do not operate in synchronous phase opposition during operation, and the entrance section end and the exit section beginning are arranged at an angle that is smaller than 180°.

13. A peristaltic fluid pump according to claim 12, wherein the pressure means comprises springs placed on opposite sides of the tube.

14. A peristaltic fluid pump according to claim 13, wherein the pressure means are disc springs.

15. A peristaltic fluid pump according to claim 12, wherein the pressure means comprises elastically deformable, curved strips made of resilient or cellular rubber.

16. A peristaltic fluid pump according to claim 13, wherein the springs are made of spring steel having a small friction factor compared to the flexible tube.

17. A peristaltic fluid pump according to claim 16, wherein the springs have sides facing the tube and wherein the springs are teflon-coated on the sides facing the tube to reduce friction.

18. A peristaltic fluid pump according to claim 13, wherein the springs are made of a plastic material.

* * * * *